| United States Patent [19] | [11] Patent Number: 4,600,775 |
| Theodoropulos | [45] Date of Patent: Jul. 15, 1986 |

[54] ISOMALEIMIDE AND ISOPHTHALAMIDE DERIVATIVES OF CHROMOPHORS

[76] Inventor: Spyros Theodoropulos, 2964 Hickory St., Yorktown Heights, N.Y. 10598

[21] Appl. No.: 644,564

[22] Filed: Aug. 27, 1984

[51] Int. Cl.$^4$ .................. C07D 265/28; C07D 237/32; C07D 311/82

[52] U.S. Cl. ...................................... 544/99; 260/377; 544/239; 549/223; 549/303; 549/321

[58] Field of Search .................. 544/99, 237; 549/223, 549/303, 321; 260/377

[56] References Cited

U.S. PATENT DOCUMENTS

| 2,998,429 | 8/1961 | Sauers et al. | 549/321 |
| 3,985,773 | 10/1976 | Alt et al. | 549/303 |
| 3,990,880 | 11/1976 | Mumford | 549/303 X |
| 4,148,625 | 4/1979 | Nagase | 549/303 X |
| 4,179,444 | 12/1979 | Roth | 549/321 X |
| 4,472,190 | 9/1984 | Yanagi et al. | 549/303 |

FOREIGN PATENT DOCUMENTS 2017737 10/1979 United Kingdom .

*Primary Examiner*—Richard L. Raymond
*Attorney, Agent, or Firm*—William R. Moran

[57] ABSTRACT

Novel isomaleimido and isophthalimido derivatives of chromophoric compounds are provided which are useful in analytical techniques for the detection and measurement of biological compounds such as bacteria, enzymes, hormones and the like.

20 Claims, No Drawings

ISOMALEIMIDE AND ISOPHTHALAMIDE DERIVATIVES OF CHROMOPHORS

FIELD OF THE INVENTION

This invention relates in general to novel isomaleimides and isophthalimides. In one aspect, this invention relates to isomaleimides and isophthalimides which are derivatives of chromophoric compounds. In a further aspect, this invention relates to certain derivatives of chromophoric compounds which have the ability to react with a variety of organic substrates forming adducts which are useful in analytical techniques for the detection and measurement of biological compounds.

DESCRIPTION OF THE PRIOR ART

A variety of compounds have been reported in the literature as being useful in analytical techniques for the detection and measurement of biological properties and components of compounds of interest. Typical components include, among others, bacteria, viruses, enzymes, drugs and hormones. For example, it is known that fluorescent groups such as fluorescein isothiocyanate can be introduced into certain specific compounds of biological interest. However, analytical techniques employing conjugates of fluorescein isothiocyanate undergo bleaching of the conjugate when exposed to ultraviolet light resulting in rapid loss of fluorescence.

Accordingly, one or more of the following objects can be achieved by the practice of this invention. It is an object of this invention to provide novel isomaleimido and isophthalimido derivatives of chromophors. Another object of this invention is to provide novel isomaleimido and isophthalimido derivatives of chromophors which may be readily coupled to compounds of clinical or biological interest. A further object of the present invention is to provide novel isomaleimides which will exhibit distinct fluorescence exitation and emission spectra, corresponding to that of the specific class of chromophors. It is also an object of the present invention to provide isomaleimido and isophthalimido derivatives of fluorescent molecules exhibiting superior stability over the native chromophors. A still further of this invention is to provide processes for the preparation of the novel chromophoric derivatives. Another object is to provide processes for the use of the derivatives for the detection and measurement of biological compounds. These and other will readily become apparent to those skilled in the art in light of the teachings herein set forth.

SUMMARY OF THE INVENTION

In its broad aspect, the present invention is directed to novel isomaleimido and isophthalimido derivatives of chromophoric compounds, processes for their preparation and use in the measurement and detection of biological compounds.

DETAILED DESCRIPTION OF THE INVENTION

The present invention is directed to novel isomaleimido and isophthalimido derivatives of chromophoric compounds. The isomaleimido or isophthalimido moiety allows the coupling of these chromophors to a variety of biological molecules of clinical interest.

The basic structure of the isomaleimido and isophthalimido derivatives of chromphors which are prepared by the teachings of this invention are conveniently represented by the structural formulas I and II:

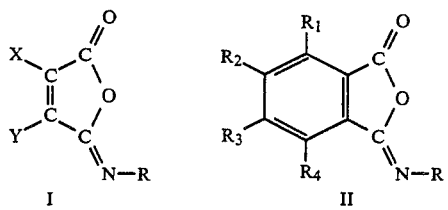

wherein R is an organic radical exhibiting chromophoric characteristics of analytical value; X and Y represent hydrogen, halogen, alkyl, aryl, alkoxy, aryloxy, nitro, amino, alkylamino, arylamino, mercapto, hydroxyl, carboxy, nitro and sulfonic groups; and $R_1$–$R_4$ represent hydrogen, halogen, carboxy, alkoxy, aryloxy, alkyl, aryl, hydroxyl, amino, alkylamino, arylamino, nitro and sulfonic groups.

Typical examples of isomaleimido and isophthalimido chromophors are shown below:

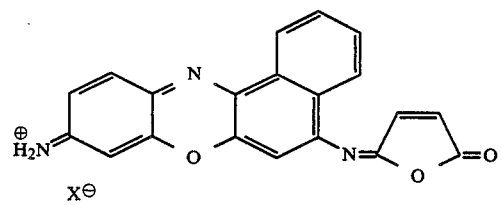
Cresyl Violet-isomaleimide

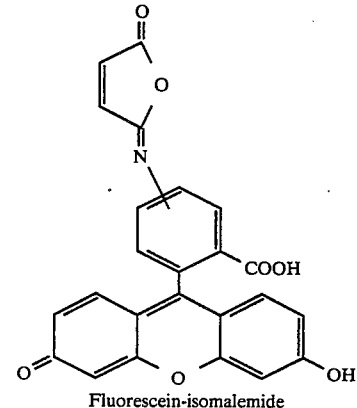
Fluorescein-isomalemide

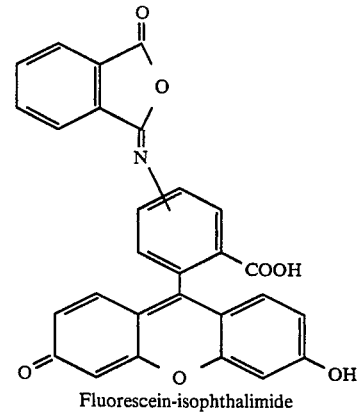
Fluorescein-isophthalimide

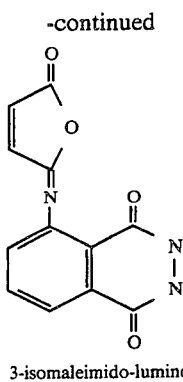

3-isomaleimido-luminol

The isomaleimido and isophthalimido compounds herein above described are conveniently synthesized in two steps using known techniques. In practice, the reaction of a chromophor having an active amine group with maleic anhydride or phthalic anhydride afford the maleamic or phthalamic acid derivative. The process of the present invention can be illustrated by the synthesis of cresyl violet-maleamic acid and cresyl-violet phthalamic acid as shown in equations III and IV, respectively:

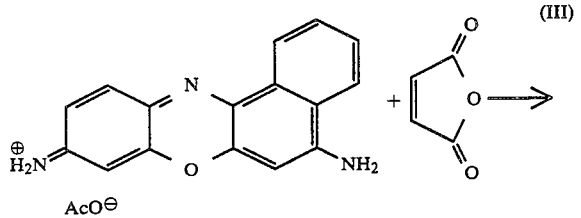

(III)

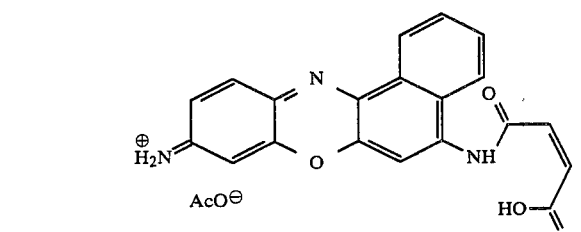

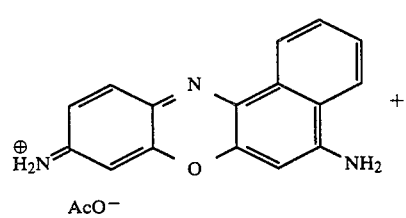

(IV)

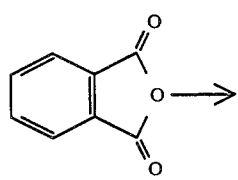

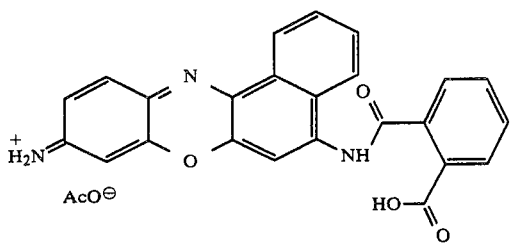

The reaction of the chromophors with maleic anhydride or phthalic anhydride is optionally performed in the presence of a solvent which is inert to the reactants and reaction products. Suitable solvents which can be employed include, among others, aliphatic or aromatic chlorinated hydrocarbons, ethers, esters, pyridine, acetic acid, amides and the like. Particularly preferred for use as the solvent is acetic acid.

The process can be conducted at temperatures of from about 5° to about 150° C. with ambient temperatures being preferred.

The resulting maleamic or phthalamic acid derivative of the chromophors are thereafter dehydrated to provide the desired isomaleimido or isophthalimido derivative.

In general, the process by which the isomaleimides and isophthalimides of the present invention are prepared is by contacting the maleamic or the phthalamic acid having the general formula V and VI:

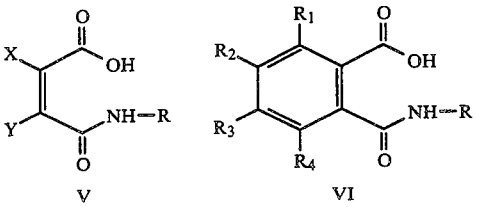

with an appropriate dehydrating agent. R in the above formulas is an organic chromophoric radical as herein before indicated; $R_1$-$R_4$ individually represent hydrogen, halogen, carboxyl, alkoxyl or aryloxy; and X and Y individually represent hydrogen, halogen, carboxyl, alkyl, aryl, alkoxy, aryloxy, hydroxyl, mercapto, alkylamino, or arylamino groups.

Illustrative dehydrating agents which can be employed in the process of this invention include, among others, acid halides, chloroformates, trifluoroacetic anhydride or carbodiimides.

The dehydration reaction is optionally performed in the presence of an organic solvent which is non-reactive with the starting materials or the desired product. Suitable organic solvents include, among others, the aromatic hydrocarbons such as benzene, toluene and the like; the halogenated aromatic hydrocarbons such as chlorobenzene and the like; cycloaliphatic hydrocarbons such as cyclohexane and the like; aliphatic hydrocarbons such as dichloromethane and the like; ethers such as diethyl ether, tetrahydrofuran, dioxane and the like; aliphatic ketones such as acetone; and dimethylformamide.

The temperature at which the reaction between the maleamic acid or the phthalamic acid and the dehydrating agent is conducted can vary over a wide range.

Temperatures from as low as about −70° C. to the temperature just below that at which decomposition of the reactants or reaction product occurs.

The dehydration step of this invention can be illustrated by the following reaction:

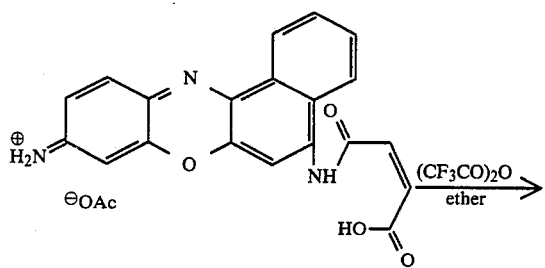

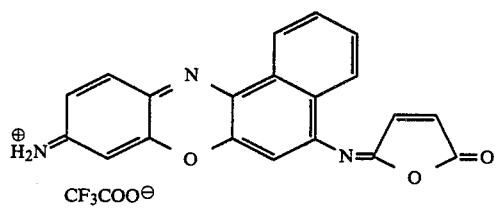

The desired derivative is then recovered by known techniques.

In another aspect of this invention the isomaleimides and isophthalimides of the general formula V and VI can react with an organic substrate containing a functional group having an active hydrogen. For example, conjugates of the chromophors of this invention and organic substrates can be conveniently represented by the formula:

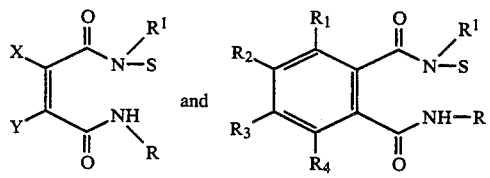

wherein R is a chromophor exhibiting fluorescence, luminescence, chemoluminescence or absorption or analytical value; S is an organic substrate containing a functional group having an active hydrogen selected from the group consisting of primary or secondary amines; $R_1$-$R_4$, and X and Y have the same values as previously indicated.

As previously indicated, the isomaleimido and isophthalimido compounds of this invention are bifunctional. The maleamic or phthalamic moieties act as ideal labeling agents due to their photochemical stability and the distinct characteristics exhibited by the same. Cresyl violet-maleamic, for example, shows an excitation at 480 nm and an emission at 580 nm, while the native chromophor exhibits an excitation at 600 nm and an emission at 630 nm. Fluorescein or fluorescein-isothiocyanate, a readily available chromphor, has been found to undergo rapid bleaching or loss of fluorescence when exposed to ultraviolet light. In contrast, the maleamic orphthalamic derivatives of this invention exhibit superior stability to ultraviolet light and undergo little or no bleaching. The isomaleimido and isophthalimido derivatives of the present invention are thus particularly useful in labeling biological compounds. It has also been observed that the compounds of the invention are also useful as staining materials for the staining of cells and as indicators.

The following examples illustrate to best mode presently contemplated for the practice of this invention.

EXAMPLE I

Preparation of N-(1-anthraquinolyl)-maleamic acid

A mixture of 2.93 grams (0.01 mols) of 1-aminoanthraquinone and 1.3 grams of maleic anhydride in 5.0 milliliters of acetic acid was stirred at ambient temperature for 3 hours. The solid product was filtered off and washed with ether. There was obtained 3.5 grams of 1-anthraquinonemaleamic acid. I.R (nujol) showed bands at 5178 (maleamic); 6.0 (carbonyl); 6.15; 6.33; 7.45; and 7.80μ.

EXAMPLE II

Preparation of 1-isomaleimidoanthraquinone 1.0 Gram of 1-anthraquinone-maleamic acid was suspended in 50 milliliters of diethyl ether. To this was added 3.0 milliters of trifluoroacetic anhydride and the mixture kept under nitrogen for 5 hours. The red maleamic acid was converted to the yellow 1-isomaleido anthraquinone. The product was filtered off and washed with ether. A total of 0.8 grams was isolated. I.R (nujol) showed bands of 5.57 (lactone); 5.90μ (imid); 5.95μ (carbonyl).

EXAMPLE III

Preparation of cresyl violet maleamic acid

A mixture of 321 mg (0.001 mols) of cresyl violet acetateand 150 mg excess of maleic anhydride in 5.0 milliliters of glacial acetic acid was stirred at ambient temperature for 24 hours. The reddish-brown solid product was filtered and washed with ether. 420 mg of the product was obtained. The product as characterized by infrared spectroscopy showed bands at (KBR) 2600 (carboxylic proton); 1685 (carboxylic); 1590 (aromatic); 1540; 1480; 1460; 1430; 1350; 1310; 1270; 1230; 11.95; 1150; and 1115 $cm^{-1}$.

EXAMPLE IV

Preparation of cresyl violet isomaleimide

420 Mg of cresyl violet-maleamic acid was suspended in 30 ml of diethylether. To this was added 1.0 milliliter of trifluoroacetic anhydride and the mixture left standing under an atmosphere of nitrogen for 15 hours. The solvent and the other volatiles were removed under reduced pressure. 390 Mg of cresyl violet-isomaleimide was obtained.

I.R (smear) showed bands of 5.58 (lactone); 5.8 ($CF_3COO$); 6.05 (imid); 6.3; 6.45; 6.9; 7.6; 8.2; 8.6μ.

Absorption $\lambda_{max}$ (in methanol) 512 nm.

Fluorescence $\lambda_{max}$ (methanol) 590 nm.

EXAMPLE V

Preparation of luminol-maleamic acid

A mixture of 1.77 grams (0.01 mol) of 3-amino phthalhydrazide and 1.5 grams of maleicanhydride in 10 milliliters of acetic acid was stirred at ambient temperature for 2 hours. The reddish product was filtered and washed with ether. 2.15 grams of luminol-maleamic acid was obtained. IR (KBR) showed bands at 3100; 3020; 2940; 2920; 2600; 1720; 1703; 1650; 1630; 1592;

1560; 1528; 1492; 1460; 1330; 1300; 1285; 1230; 1180 and 1120 cm⁻¹.

EXAMPLE VI

Preparation of Luminol-isomaleimide 1.0 Gram of luminol-maleamic acid was suspended in 50 ml of diethyl ether. To this was added 3.0 milliliters of trifluoroacetic anhydride and the mixture stirred under nitrogen for 2 hours. A yellow crystalline product was obtained which was filtered and washed with ether. The product was characterized by infrared spectroscopy and showed bands at (KBR) 1810 (lactone); 1770; 1728 (hydrazide carbonyl); 1678 (imid); 1635; 1605; 1590; 1525; 1330; and 1283 cm⁻¹.

EXAMPLE VII

Preparation of Fluorescein-5-maleamic acid

A mixture of 350 milligrams (0.001 mols) of 5-aminofluorescein and 300 milligrams (excess) of maleic anhydride were mixed in 5.0 milliliters of glacial acetic acid and the mixture was stirred at ambient temperature for 24 hours. The yellow product formed was filtered off and washed three times with diethyl ether. 420 Milligrams of fluorescein-maleamic acid was obtained. I.R (KBR) showed bands at 2.55; 3.28; 3.38; 4.05; 5.85; 6.30; 6.52; 6.88; 6.90; 7.70; 8.34; 8.52; and 8.30μ.

EXAMPLE VIII

Preparation of 5-isomaleimido-fluorescein 200 mg of fluorescein maleamic acid was suspended in 30 milliliters of diethylether. To this was added 1.0 milliliters of trifluoroacetic anhydride and the mixture was stirred under an atmosphere of nitrogen for one hour. The homogeneous solution was evaporated to dryness. 168 mg of isomaleimido-fluorescein was obtained. I.R (smear) showed bands at 3.5 (COOH); 5.60 (lactone); 5.8 (carbonyl); 6.10 (imid); 6.2; 6.45; 6.68; 7.00; 8.30μ.

EXAMPLE IX

Preparation of fluoresceinphthalamic acid

A mixture of 350 mg (0.001 mol) of 5-aminofluorescein and 200 mg of phthalic anhydride in 5 milliliters of glacial acetic acid was stirred at ambient temperature for 48 hours. The yellow reddish product was filtered and washed once with acetic acid and twice with diethyl ether. 460 Mg of fluorescein-phthalamic acid was obtained. I.R (KBR) showed bands at 3060; 3000; 1685; 1590; 1540; 1480; 1460; 1430; 1350; 1310; 1270; 1230; 1195; 1150; and 1115 cm⁻¹.

Although the invention has been illustrated by the preceding examples, it is not to be construed as being limited to the materials employed therein, but rather, the invention encompasses the generic area as hereinbefore disclosed. Various modifications and embodiments thereof can be made without departing from the spirit and scope thereof.

What is claimed is:

1. A compound selected from the group consisting of:

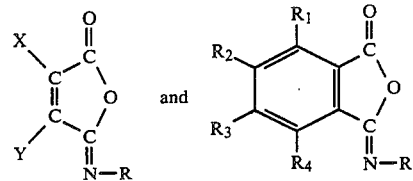

wherein R represents an organic chromophoric group exhibiting fluorescence, luminescense, chemoluminescence or absorption properties; $R_1$, $R_2$, $R_3$, and $R_4$ individually represent hydrogen or halogen, or alkyl, aryl, hydroxyl, carboxyl, alkyl or aryl-substituted or unsubstituted amino groups, nitro or sulfonic groups; and X and Y represent hydrogen or halogen, or alkyl, aryl, alkoxy, aryloxy, carboxyl, hydroxyl, alkyl or aryl-substituted or unsubstituted amino groups, nitro or sulfonic groups with the proviso that R does not contain a group of the formula:

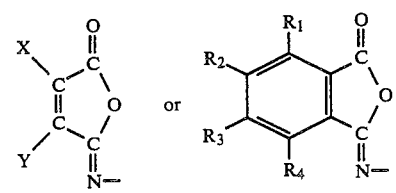

wherein $R_1$–$R_4$, X and Y are as indicated above.

2. The compound of claim 1 which is an N-substituted isomaleimide of the formula:

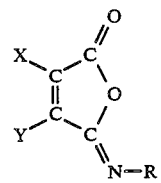

wherein R, X and Y are as indicated.

3. The compound of claim 1 which is an N-substituted isophthalimide of the formula:

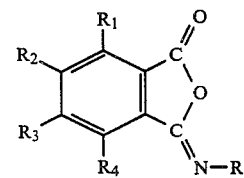

wherein R–$R_4$ are as indicated.

4. The compound of claim 1 wherein said R group exhibits fluorescence properties.

5. The compound of claim 1 wherein said R group exhibits luminescence properties.

6. The compound of claim 1 wherein said R group exhibits chemoluminescence properties.

7. The compound of claim 1 wherein said R group exhibits absorption properties.

8. A compound of the formula:

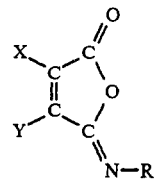

wherein R represents a cresyl-violet group; and X and Y represent hydrogen or halogen, or alkyl, aryl, alkoxy, aryloxy, carboxyl, hydroxyl, or alkyl- or aryl-substituted or unsubstituted amino groups or nitro or sulfonic groups.

9. A compound of the formula:

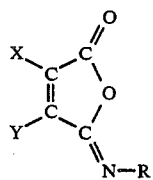

wherein R represents an anthraquinone group; and X and Y represent hydrogen or halogen, or alkyl, aryl, alkoxy, aryloxy, carboxyl, hydroxyl, or alkyl- or aryl-substituted or unsubstituted amino groups, or nitro or sulfonic groups.

10. A compound of the formula:

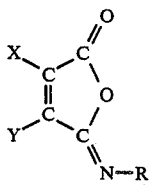

wherein R represents a fluorescein group; and X and Y represent hydrogen or halogen, or alkyl, aryl, alkoxy, aryloxy, carboxyl, hydroxyl, or alkyl- or aryl-substituted or unsubstituted amino groups, or nitro or sulfonic groups.

11. A compound of the formula:

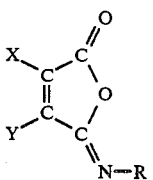

wherein R represents a luminol group; and X and Y represent hydrogen or halogen, or alkyl, aryl, alkoxy, aryloxy, carboxyl, hydroxyl, or alkyl- or aryl-substituted or unsubstituted amino groups, or nitro or sulfonic groups.

12. A compound of the formula:

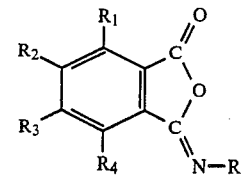

wherein R represents a flourescein group; $R_1$, $R_2$, $R_3$ and $R_4$ individually represent hydrogen or halogen, or alkyl, aryl, hydroxyl, carboxyl, alkyl- or aryl-substituted or unsubstituted amino groups, nitro or sulfonic groups; and X and Y represent hydrogen or halogen, or alkyl, aryl, alkoxy, aryloxy, carboxyl, hydroxyl, or alkyl- or aryl-substituted or unsubstituted amino groups, or nitro or sulfonic groups.

13. A compound selected from the group consisting of:

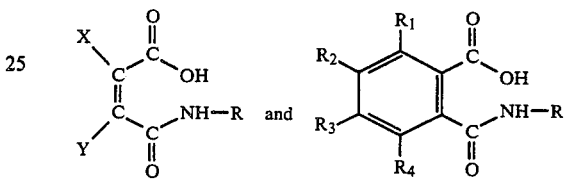

wherein R represents an organic chromophoric group exhibiting fluorescence, luminescense, chemoluminescence or absorption properties; $R_1$, $R_2$, $R_3$, and $R_4$ individually represent hydrogen or halogen, or alkyl, aryl. hydroxyl, carboxyl, alkyl or aryl-substituted or unsubstituted amino groups, nitro or sulfonic groups; and X and Y represent hydrogen or halogen, or alkyl, aryl. alkoxy, aryloxy, carboxyl, hydroxyl, alkyl- or aryl-substituted or unsubstituted amino groups, nitro or sulfonic groups with the proviso that R does not contain a group of the formula:

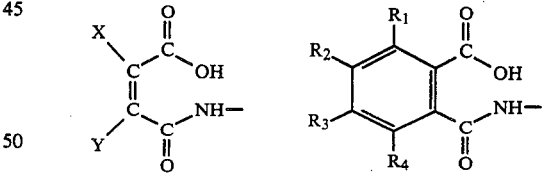

wherein $R_1$-$R_4$, X and Y are as indicated above.

14. The compound of claim 13 which is a maleamic acid of the formula:

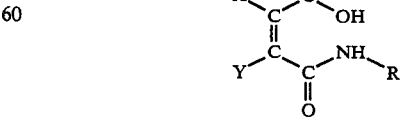

wherein R, X and Y are as indicated.

15. The compound of claim 13 which is a phthalamic acid of the formula:

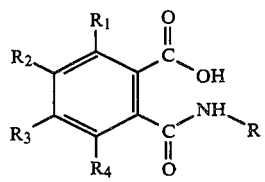

wherein R–R$_4$ are as indicated.

16. A compound of the formula:

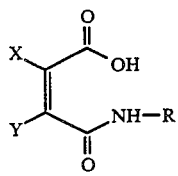

wherein R represents a cresyl-violet group; and X and Y represent hydrogen or halogen, or alkyl, aryl, alkoxy, aryloxy, carboxyl, hydroxyl, or alkyl- or aryl-substituted or unsubstituted amino groups, or nitro or sulfonic groups.

17. A compound of the formula:

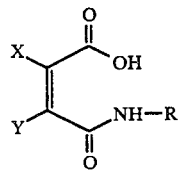

wherein R represents an anthraquinone group; and X and Y represent hydrogen or halogen, or alkyl, aryl, alkoxy, aryloxy, carboxyl, hydroxyl, or alkyl- or aryl-substituted or unsubstituted amino groups, or nitro or sulfonic groups.

18. A compound of the formula:

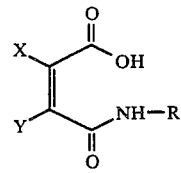

wherein R represents a fluorescein group; and X and Y represent hydrogen or halogen, or alkyl, aryl, alkoxy, aryloxy, carboxyl, hydroxyl, or alkyl- or aryl-substituted or unsubstituted amino groups, or nitro or sulfonic groups.

19. A compound of the formula:

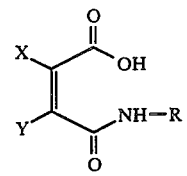

wherein R represents a luminol group; and X and Y represent hydrogen or halogen, or alkyl, aryl, alkoxy, aryloxy, carboxyl, hydroxyl, or alkyl- or aryl-substituted or unsubstituted amino groups, or nitro or sulfonic groups.

20. A compound of the formula:

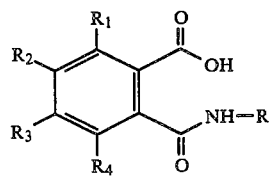

wherein R represents a fluorescein group; R$_1$, R$_2$, R$_3$ and R$_4$ individually represent hydrogen or halogen, or alkyl, aryl, hydroxyl, carboxyl, alkyl- or aryl-substituted or unsubstituted amino groups, nitro or sulfonic groups; and X and Y represent hydrogen or halogen, or alkyl, aryl, alkoxy, aryloxy, carboxyl, hydroxyl, or alkyl- or aryl-substituted or unsubstituted amino groups, or nitro or sulfonic groups.

* * * * *